US009596834B2

(12) United States Patent
Yoneyama et al.

(10) Patent No.: US 9,596,834 B2
(45) Date of Patent: Mar. 21, 2017

(54) STEATOHEPATITIS-LIVER CANCER MODEL ANIMAL

(71) Applicant: STELIC INSTITUTE OF REGENERATIVE MEDICINE, STELIC INSTITUTE & CO., Tokyo (JP)

(72) Inventors: Hiroyuki Yoneyama, Tokyo (JP); Masato Fujii, Tokyo (JP)

(73) Assignee: Stelic Institute of Regenerative Medicine, Stelic Institute & Co., Tokyo (JP)

(*) Notice: Subject to any disclaimer, the term of this patent is extended or adjusted under 35 U.S.C. 154(b) by 0 days.

(21) Appl. No.: 14/191,942

(22) Filed: Feb. 27, 2014

(65) Prior Publication Data
US 2014/0178306 A1 Jun. 26, 2014

Related U.S. Application Data

(63) Continuation of application No. 13/319,851, filed as application No. PCT/JP2009/063675 on Jul. 31, 2009, now abandoned.

(51) Int. Cl.
*A01K 67/00* (2006.01)
*A01K 67/027* (2006.01)

(52) U.S. Cl.
CPC ........ *A01K 67/027* (2013.01); *A01K 2207/20* (2013.01); *A01K 2207/25* (2013.01); *A01K 2227/10* (2013.01); *A01K 2267/0331* (2013.01)

(58) Field of Classification Search
None
See application file for complete search history.

(56) References Cited

U.S. PATENT DOCUMENTS

2007/0265323 A1   11/2007   Sharma et al.

FOREIGN PATENT DOCUMENTS

| EP | 2238987 | 10/2010 |
|---|---|---|
| JP | 2000-270713 | 10/2000 |
| JP | 2004-141043 | 5/2004 |
| WO | 2009/084232 | 7/2009 |

OTHER PUBLICATIONS

Hemmings et al., The International Journal of Biochemistry & Cell Biology, 2000; 32:905-919.*
Anstee et al., "Mouse models in non-alcoholic fatty liver disease and steatohepatitis research" Int J Exp Pathol. (Feb. 2006) 87(1):1-16.
De La Monte et al., "Epidemiological Trends Strongly Suggest Exposures as Etiologic Agents in the Pathogensis of Sporadic Alzheimer's Disease, *Diabetes mellitus*, and Non-Alcoholic Steatohepatitis" J Alzheimers Dis. (2009) 17 (3):519-29.
Fujii et al., "A murine model for non-alcoholic steatohepatitis showing evidence of association between diabetes and hepatocellular carcinoma" Med Mol Morphol. (Sep. 2013) 46(3):141-52.
Horie et al., "Hepatocyte-specific Pten deficiency results in steatohepatitis and hepatocellular carcinomas" The Journal of Clinical Investigation (Jun. 2004) 113(12):1774-1783.
International Search Report for PCT/JP2009/063675 dated Aug. 25, 2009.
Iwai et al., "High sensitivity of fatty liver Shionogi (FLS) mice to diethylnitrosamine hepatocarcinogenesis: Comparison to C3H and C57 mice" Cancer Lett. (Feb. 8, 2007) 246(1-2):115-21.
Kunhathoor et al., "Increased Atherosclerosis in Streptozotocin-induced Diabetic Mice" J. Clin. Invest. (1996) 97:1767-1773.
Larter et al., "Animal models of NASH: Getting both pathology and metabolic context right" J Gastroenterol Hepatol. (Nov. 2008) 23(11):1635-48.
Miyamoto et al. "Hepatic changes in adenine nucleotide levels and adenosine 3'-monophosphate forming enzyme in streptozotocin-induced diabetic mice" The Journal of Toxicological Sciences (2008) 33(2):209-217.
Reed et al., "A New Rat Model of Type 2 Diabetes: The Fat-Fed, Streptozotocin-Treated Rat" Metabolism. (Nov. 2000) 49(11):1390-4.
Rinella et al., "The methionine-choline deficient dietary model of steatohepatitis does not exhibit insulin resistance" Journal of Hepatology (2004) 40:47-51.
Sahai et al., "Obese and diabetic db/db mice develop marked liver fibrosis in a model of nonalcoholic steatohepatitis: role of short-form leptin receptors and osteopontin" Am J Physiol Gastrointest Liver Physiol (2004) 287:G1035-G1043.
Shankar et al., "Streptozotocin-induced diabetic mice are resistant to lethal effects of thioacetamide hepatotoxicity" Toxicology and Applied Pharmacology (2003) 188:122-134.
Wang et al., "Enhanced Hepatotoxicity and Toxic Outcome of Thioacetamide in Streptozotocin-Induced Diabetic Rats" Toxicology and Applied Pharmacology (2000) 166:92-100.
Yanagitani et al., "Retinoic Acid Receptor alpha Dominant Negative Form Causes Steatohepatitis and Liver Tumors in Transgenic Mice" Hepatology (2004) 40(2):366-375.

* cited by examiner

*Primary Examiner* — Doug Schultz
(74) *Attorney, Agent, or Firm* — Karl Bozicevic; Bozicevic, Field & Francis LLP

(57) ABSTRACT

Fatty liver was induced by administering agents for inducing organ inflammation to experimental animals to evoke insulin resistance and by rearing them with high-fat diets. As a result, steatohepatitis was successfully induced in the animals. The animals show pathological findings similar to those of humans. By using these model animals, substances for treating or preventing diseases can be efficiently screened and the efficacy of medicinal substances can be effectively evaluated.

11 Claims, 11 Drawing Sheets

1. PANCREAS

2w x400

4w x400

2. ADIPOSE TISSUE

2w

6w

4w

1. HISTOLOGICAL ANALYSIS

2. GENE EXPRESSION ANALYSIS

1. DIABETIC NEPHROPATHY

2. DIABETIC RETINOPATHY
(IMMUNOSTAINING IMAGES OF NEW BLOOD VESSEL, CD31)

STEATOHEPATITIS-LIVER CANCER MODEL ANIMAL

TECHNICAL FIELD

The present invention relates to steatohepatitis/liver cancer model animals, and uses thereof.

BACKGROUND ART

Previously, non-alcoholic fatty liver disease was believed to be a benign disease that does not progress. However, it was revealed that even non-drinkers develop inflammation similar to alcoholic hepatitis and show hepatic fibrosis histology, and now the non-alcoholic fatty liver disease is known as a disease with poor prognosis. In particular, metabolic syndromes due to obesity, diabetes, or the like have been drawing attention in recent years. It is becoming a common view that nonalcoholic steatohepatitis (NASH) is one of such syndromes. However, the mechanism remains unclear, and effective methods and/or agents for treating NASH have not been established. This is partly because NASH is due to human lifestyle-related diseases, and thus appropriate experimental animals have not been established.

For the development of effective methods and agents for treating NASH, it is essential to elucidate the pathological condition of NASH, which progresses to lethal diseases such as liver cirrhosis and liver cancer. However, experimental animals that are currently used as a NASH model mouse in research include single-gene modified mice such as leptin receptor-deficient mice (Non-patent Document 1), hepatocyte-specific Pten-deficient mice (Non-patent Document 2), and retinoic acid receptor α dominant-negative transgenic mice (Non-patent Document 3), and mice induced with a special diet such as a methionine/choline-deficient diet (Non-patent Document 4). However, the human pathogenesis differs from that in the genetically-modified mice in which a single-gene mutation is responsible for the development and progression of the pathological condition, and is unlikely to be due to only the intake of a particular nutrient. Furthermore, insulin resistance and hepatic fibrosis cannot be simultaneously monitored in these mice. Furthermore, the ALT, an index in serobiochemical analysis, is only slightly elevated in mice that develop fibrosis, and therefore several mouse tissue slices are required to assess their pathological condition. Conversely, the pathological condition is assumed to be different from that of human because ALT is elevated to a markedly high level. Furthermore, the pathological condition recovers spontaneously after treatment. This makes it difficult to test and assess drugs for their efficacy. Thus, for developing methods and agents for treating NASH, it is desirable to establish an experimental animal model that is compatible with the human clinical condition.

Although various studies have been conducted, there is no experimental animal exhibiting pathological conditions similar to those of human. Thus, under the current circumstances, it is difficult to conduct detailed screening to elucidate the pathogenesis or to establish therapeutic methods.

PRIOR ART DOCUMENTS

[Non-patent Document 1] Sahai A et al., Am J Physiol Gastroentest Liver Physiol 287: G1035, 2004
[Non-patent Document 2] Horie Y et al., J Clin Invest 113: 1774, 2004
[Non-patent Document 3] Yanagitani A et al., Hepatology 40: 366, 2004
[Non-patent Document 4] Rinella M et al., Journal of Hepatology 40: 47, 2004

SUMMARY OF THE INVENTION

Problems to be Solved by the Invention

An objective of the present invention is to provide steatohepatitis model animals and liver cancer model animals that exhibit pathological findings similar to those of humans, and uses thereof. More specifically, an objective of the present invention is to provide techniques for producing model animals that develop into fatty liver, steatohepatitis, hepatic fibrosis, liver cirrhosis, and liver cancer from insulin resistance.

Means for Solving the Problems

The present inventors conducted dedicated studies to achieve the above-described objectives. The present inventors induced insulin resistance by administering an agent for inducing organ inflammation, and induced fatty liver in mice by feeding them with a high fat diet. As a result, the present inventors successfully developed steatohepatitis in mice. A detailed observation of the mice revealed the following pathological findings:

(1) macrovesicular fat deposition in liver cells and liver cell ballooning;
(2) infiltration of inflammatory cells; and
(3) fibrosis around mainly the central vein.

The above-described pathological findings are characteristic of human nonalcoholic steatohepatitis (NASH). Specifically, by using the above-described method, the present inventors for the first time successfully produced mice that exhibit similar pathological findings as those of human NASH.

The NASH animal model produced by the present inventors is different from conventional animal models in the following points:

(1) similarly to that observed in the histophathological findings of human, fatty degeneration and fibrosis of liver cells progress mainly around the central vein instead of the portal vein; and
(2) the histophathological images of human "burned-out NASH" are observed, in which only hepatic fibrosis is seen, although fat deposition and loss of inflammatory cells are observed as the pathological condition progresses.

The animal model of the present invention is characteristic in that it is produced without genetic modification. Furthermore, the model animals of the present invention unfailingly (100%) develop a pathological condition similar to the progression and prognosis of human NASH at a constant time course, and are the first model animals that exhibit the same course of progression of pathological condition in human. In addition, the model animals of the present invention have a remarkably beneficial effect in that all of insulin resistance, fatty liver, steatohepatitis, hepatic fibrosis, and liver cirrhosis can be observed at the same time.

Moreover, the present inventors newly found that the above-described NASH model animals develop liver cancer following liver cirrhosis as they continue the rearing. This is the same change of pathological condition observed in humans. Thus, the animals prepared by the methods of the present invention are very useful as model animals of human liver cancer.

Human liver cancer causes the liver surface to bulge. However, conventional model animals for liver cancer, which are prepared by administering a chemical substance, develop liver cancer that does not cause bulging of the liver surface. Meanwhile, model animals of the present invention, which are prepared without genetic modification and drug administration, exhibit bulging of the liver surface in a fashion similar to the case of human liver cancer. Thus, the model of the present invention is a model much closer to human liver cancer. Furthermore, liver cirrhosis is not developed by administering chemical substances, while model animals of the present invention develop massive type cord-like liver cell carcinoma. Furthermore, infiltration of inflammatory cells and development of liver cancer caused by cirrhosis to displace normal liver cells are observed in the model animals of the present invention. In the model, the origin of liver cancer is macrovesicular fatty liver which shows a pathological condition very similar to that of human NASH. The liver cancer develops from hepatic fibrosis and liver cirrhosis. Thus, the animal model of the present invention is very useful, as it has not been reported previously.

As described above, the present inventors successfully produced model animals for steatohepatitis and liver cancer which show similar pathological findings to those of human, and thereby completed the present invention. By using these model animals, it is possible to efficiently screen for substances for treating or preventing diseases, and effectively evaluate the efficacy of medicinal substances.

The present invention relates to model animals which develop into fatty liver, steatohepatitis, hepatic fibrosis, cirrhosis, and liver cancer from insulin resistance, and more specifically, the present invention provides:

[1] A non-human animal model for steatohepatitis produced by administering an agent for inducing organ inflammation;
[2] The non-human animal of [1], wherein the steatohepatitis is a non-alcoholic steatohepatitis;
[3] a non-human animal model for diabetes produced by administering an agent for inducing organ inflammation;
[4] the non-human animal of any one of [1] to [3], wherein the agent for inducing organ inflammation is an N-acetyl-β-D-glucosaminidase inhibitor;
[5] the non-human animal of any one of [1] to [4], which comprises the step of inducing fatty liver by administering an agent for inducing organ inflammation to the animal and rearing the animal with a high-fat diet;
[6] the non-human animal of any one of [1] to [5], wherein the non-human animal is a mouse;
[7] a method of producing a non-human animal model of steatohepatitis, which comprises the step of inducing inflammation in an organ of the non-human animal;
[8] a method of screening for a substance for treating or preventing steatohepatitis, which comprises the steps of:
(a) administering a test substance to the non-human animal model of steatohepatitis of [1]; and
(b) evaluating an ameliorating effect on steatohepatitis;
[9] a method of evaluating a medicinal substance for efficacy against steatohepatitis amelioration, which comprises the steps of:
(a) administering a test medicinal substance to the non-human animal model of steatohepatitis of [1]; and
(b) evaluating an ameliorating effect on steatohepatitis;

[10] a method of screening for a substance for treating or preventing a diabetic disorder, which comprises the steps of:
(a) administering a test substance to the non-human animal model for a diabetic disorder of [3]; and
(b) evaluating an ameliorative effect on diabetic disorder;
[11] a method of evaluating the side effects risks of a pharmaceutical agent for treating or preventing a diabetic disorder, which comprises the steps of:
(a) administering a test pharmaceutical agent to the non-human animal model for a diabetic disorder of [3]; and
(b) evaluating the pharmaceutical agent for treating or preventing diabetic disorder for side effects;
[12] a non-human animal model for liver cancer, which is produced by further rearing the non-human animal of any one of [1] to [6];
[13] the non-human animal of [12], which is structurally characterized by the following pathological morphology:
(a) massive type cord-like liver cell carcinoma;
(b) infiltration of inflammatory cells; or
(c) liver cancer caused by cirrhosis developed such that it displaces normal liver cells;
[14] a method of screening for a substance for treating or preventing liver cancer, which comprises the steps of:
(a) administering a test substance to the non-human animal model for liver cancer of [12] or [13]; and
(b) evaluating a therapeutic effect on liver cancer; and
[15] a method of evaluating a medicinal substance for efficacy against liver cancer treatment, which comprises the steps of:
(a) administering a test medicinal substance to the non-human animal model of liver cancer of [12] or [13]; and
(b) evaluating a therapeutic effect on liver cancer.

[Effects of the Invention]

To produce experimental animals that develop pathological conditions similar to those of humans, insulin resistance was induced in mice, and fatty liver was induced by feeding them with a high fat diet.

Mice of different ages were sacrificed and each organ, mainly liver, was analyzed histopathologically (HE staining, fat staining, immunostaining for macrophages and fibroblasts). NAFLD Activity Score (NAS; reference: "Kleiner D E et al., Hepatology. 2005 June; 41(6): 1313-21") was calculated to assess the pathological features in detail. Model animals of the present invention can also be assessed for NASH by using the same NAFLD Activity Score as for human. Thus, the model animals of the present invention are very useful as NASH model animals.

Furthermore, serobiochemical tests were carried out using FUJIFILM DRI-CHEM. Gene expression analysis was performed using Real-Time RT-PCR (Takara).

As described above, the present inventors successfully produced steatohepatitis model animals (for example, NASH model animals) and liver cancer model animals that show pathological findings similar to those of humans.

The present invention provides simple techniques for stably producing animals that develop at an early stage a pathological condition similar to human NASH, which leads to fatty liver, steatohepatitis, hepatic fibrosis, and liver cirrhosis, followed by spontaneous development of liver cancer as a result of progression of the pathological condition, by inducing insulin resistance in experimental animals such as mice, and loading them with a high fat diet.

Furthermore, diabetic disorders (diabetic nephritis, retinopathy, hyperlipidemia, and arteriosclerosis) can also be simultaneously observed in the animals. Thus, the present invention also provides techniques for producing experimental animals that enable the pathological conditions of metabolic syndrome to be observed at the same time.

Meanwhile, in ob/ob mice and db/db mice which are commonly used as an NASH model, the pathological condition does not develop uniformly with aging. It is necessary to monitor the pathological condition of the mice to accurately assess the disease state of NASH, which makes the experiments cumbersome and complicated. Furthermore, the pathological lesions are not always irreversible. This has made the efficacy assessment difficult (Horie Y et al., J din Invest 113: 1774-1783, 2004; Yanagitani A et al., Hepatology 40: 366-375, 2004; Anstee Q M et al., Int J Exp Path 87: 1-16, 2006). Meanwhile, in the model animals of the present invention, the period leading to the mature pathological condition is constant and its progression is irreversible. Thus, the model animals of the present invention can be used to solve the above-described problems.

The model animals of the present invention can be used in preclinical tests for various therapeutic agents, and are very useful in developing agents and searching for therapeutic targets.

MODE FOR CARRYING OUT THE INVENTION

Figure 1:
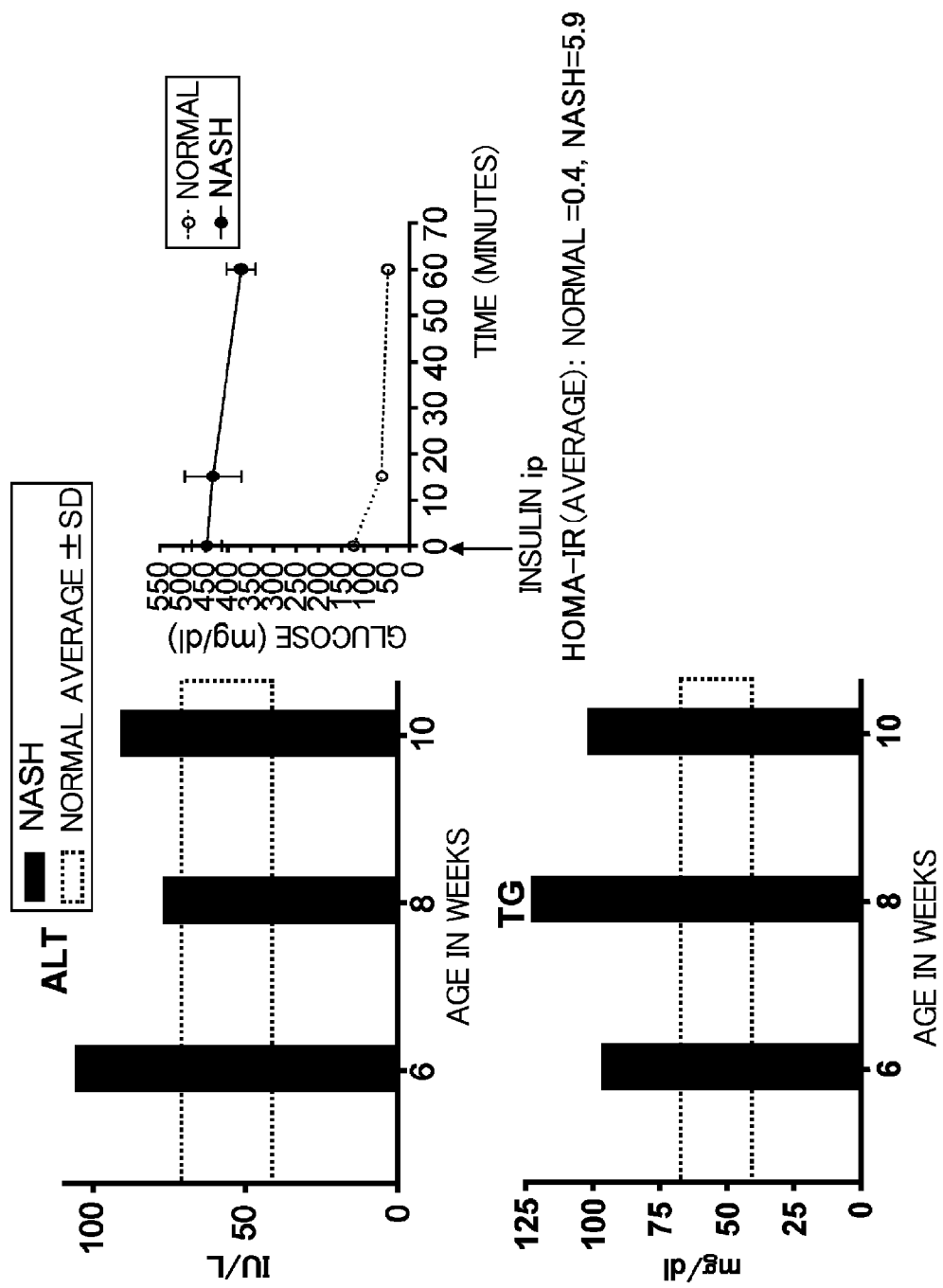
FIG. 1 shows a result of serobiochemical test in mice of the present invention.

The present invention relates to steatohepatitis model animals produced by inducing insulin resistance.

In a preferred embodiment, the present invention provides steatohepatitis model animals (herein sometimes referred to as "model animals of the present invention") prepared by administering agents for inducing organ inflammation.

Model animals of the present invention are prepared by administering to experimental animals agents for inducing organ inflammation and then preferably feeding them with high fat diets.

Animals to be used in the present invention are not particularly limited, as long as they are commonly used as experimental animals. Such animals typically include non-human animals, preferably non-human vertebrates, more preferably non-human mammals, and still more preferably rodents. Examples of animals that can be used to prepare model animals of the present invention specifically include mice, rats, rabbits, dogs, chickens, and monkeys (such animals are sometimes also referred to simply as "experimental animals").

The genetic background of the animals to be used to produce model animals of the present invention is not particularly limited; and it is possible to use animals with any genetic background. In general, wild-type animals can be preferably used.

In the present invention, the agents for inducing organ inflammation (herein sometimes also referred to simply as "agents") are not particularly limited, as long as they have an activity of directly or indirectly inducing inflammation in various organs. Organs for inducing inflammation include, for example, pancreas, adipose tissues, and muscle tissues. The agents for inducing organ inflammation of the present invention also include agents that directly or indirectly induce inflammation in the peripheral tissues.

The agents for inducing organ inflammation of the present invention preferably include N-acetyl-β-D-glucosaminidase inhibitors.

In a preferred embodiment, model animals of the present invention are produced by administering N-acetyl-β-D-glucosaminidase inhibitors to the above-described experimental animals. Such inhibitors include, for example, streptozotocin and Pugnac.

Alternatively, nucleic acids having an activity of inhibiting N-acetyl-β-D-glucosaminidase can also be used as an agent of the present invention. Specifically, such nucleic acids include, for example, siRNAs that suppress the expression of the O-GlcNAcase gene (GenBank accession No. NM_023799.3), antisenses of the gene, and ribozymes that target the gene.

In producing the model animals of the present invention, the dosage form of the agents for inducing organ inflammation is not particularly limited. For example, the dosage form includes, for example, subcutaneous administration (subcutaneous injection, etc.), intravenous administration, oral administration, and intraperitoneal administration.

The dose of the agent to be administered is not limited, and is typically 50 to 500μg, preferably 100 to 300μg, and more preferably 200μg when the agent is streptozotocin.

The timing for administering the agent is as follows. The agent is typically administered one to five days after birth (neonatal period, preferably one to five days old, and more preferably two days old), and preferably two days after birth.

As described above, insulin resistance can be induced by administering the agents. After administration of the agents as described above, the animals are reared to produce model animals of the present invention. In general, the animals are preferably fed with a high fat diet. Such high fat diets include various general animal diets that are commercially available.

The major ingredients of the above-described high fat diets include, for example, crude fat, crude protein, crude fiber, crude ash, nitrogen-free extract, and water. The high fat diets of the present invention are not particularly limited; however, the content of crude fat is 20% or more, and preferably 30% or more; and the ratio of fat-derived calories to total calories is typically 50% or more, and preferably 60% or more. Ingredients to be formulated into the high fat diets include, for example, powdered beef tallow, milk casein, powdered egg white, L-cystine, safflower oil, crystalline cellulose, maltodextrin, lactose, and sucrose. These substances are shown as an example of ingredients of the high fat diets, and are not necessarily contained in the diets.

The above-described high fat diets include, but are not limited to, for example, those that have a higher content of crude fat (for example, higher by about 30% or more) than normal diets. An example of such high fat diets include those commercially available as diets for laboratory animals, such as High Fat Diet32 (CLEA Japan Inc.) and D12492 (Research Diets).

For example, when the animals are mice, the above-described high fat diet feeding begins typically at the age of 2 to 6 weeks, preferably 3 to 5 weeks, and more preferably 4 weeks. In addition, for example, in the case of mice, the amount of high fat diet given each time is about 3 to 6 g. In general, mice are preferably fed with the high fat diet for one week or more. Those skilled in the art can appropriately regulate (adjust) the amount of high fat diet depending on the type, size, weight, or such of the experimental animals to be used. Fatty liver can be induced by feeding them with a high fat diet. Thus, in a preferred embodiment, the present invention provides steatohepatitis model animals, which comprise the step of inducing fatty liver by administering to the animals agents for inducing organ inflammation and by feeding them with a high fat diet.

Animals produced by the above-described method develop symptoms of steatohepatitis and are useful as steatohepatitis model animals. The model animals of the present invention have the characteristic of simultaneously developing pathological conditions that are observed in animals prepared by the methods of the present invention. It is preferred that the model animals simultaneously develop insulin resistance and/or hepatic fibrosis. However, such pathological conditions are not limited to these examples.

In a preferred embodiment, the model animals of the present invention are characteristic in that the pathological conditions of metabolic syndrome can be observed at the same time, since diabetic disorders (diabetic nephritis, retinopathy, hyperlipidemia, and arteriosclerosis) can be observed simultaneously in model animals of the present invention.

Furthermore, since the model animals of the present invention have the characteristic that pathological condition does not recover spontaneously, the animals can be suitably used in testing and assessing drug efficacy.

In a preferred embodiment of the model animals of the present invention, the above-described steatohepatitis is nonalcoholic hepatitis (NASH). Specifically, the present invention provides nonalcoholic hepatitis (NASH) model animals, which are prepared by administering agents for inducing organ inflammation. The animals steadily develop in a constant time course pathological conditions with similar progression and prognosis to those of human NASH.

In a preferred embodiment, nonalcoholic hepatitis model animals of the present invention have at least one (preferably, all) of the following pathological findings:
(1) macrovesicular fat deposition in liver cells and liver cell ballooning;
(2) infiltration of inflammatory cells; and
(3) fibrosis around mainly the central vein.

Accordingly, in a preferred embodiment, model animals of the present invention are structurally characterized by the above-described pathological morphologies.

As the rearing continued, the above-described steatohepatitis model animals of the present invention developed liver cirrhosis which led to liver cancer. Thus, steatohepatitis model animals of the present invention are also useful, for example, as animals (starting materials) for producing liver cirrhosis model animals or liver cancer model animals Specifically, the present invention provides materials for preparing liver cirrhosis or liver cancer model animals, which comprise steatohepatitis model animals of the present invention.

Furthermore, methods for producing model animals of the present invention as described above are also included in the present invention. In a preferred embodiment, the present invention provides methods for producing steatohepatitis model animals, which comprise the step of administering agents for inducing organ inflammation to non-human animals Furthermore, substances for treating or preventing steatohepatitis can be screened by using model animals of the present invention. Specifically, the present invention provides methods of screening for substances for treating or preventing steatohepatitis, which comprise the steps of:
(a) administering a test substance to a steatohepatitis model animal of the present invention; and
(b) evaluating its ameliorating effect on steatohepatitis.

Test substances to be used in these methods are not particularly limited. For example, such substances include single compounds such as natural compounds, organic compounds, inorganic compounds, proteins, and peptides, as well as compound libraries, expression products of gene libraries, cell extracts, cell culture supernatants, products of fermenting microorganisms, extracts of marine organisms, and plant extracts, but are not limited thereto.

Methods for administering test substances or medicinal substances of the present invention are not particularly limited; however, they can be administered, for example, orally or by injection. When such a test substance is a protein, for example, a viral vector carrying a gene encoding the protein may be constructed and can be introduced into model animals of the present invention using their infectability.

In the step of (b), the ameliorating effect on steatohepatitis can be evaluated by determining whether steatohepatitis is ameliorated by assessing the pathological findings of the model animals.

The pathological findings of steatohepatitis include, for example, the above-described pathological findings (pathological morphologies). Herein, "amelioration" means that the symptoms of steatohepatitis are alleviated or restored to normal. By using as an indicator the pathological findings described herein, those skilled in the art can appropriately evaluate whether the symptoms of steatohepatitis are ameliorated in the model animals.

In the present invention, substances that produce the ameliorating effect in the step of (b) above can be selected as substances for treating or preventing steatohepatitis.

Furthermore, medicinal substances can be assessed for their efficacy in ameliorating steatohepatitis by using model animals of the present invention. Specifically, the present invention provides methods for evaluating the efficacy of medicinal substances in ameliorating steatohepatitis, which comprise the steps of:
(a) administering a test medicinal substance to a steatohepatitis model animal of the present invention; and
(b) evaluating its ameliorating effect on steatohepatitis.

The type of medicinal substances that can be evaluated for efficacy by the above-described methods is not particularly limited; and such medicinal substances include, for example, various known pharmaceutical agents (low-molecular-weight compounds, proteins, nucleic acids, or such).

When a test medicinal substance exerts an ameliorating effect on steatohepatitis, the medicinal substance is judged to have therapeutic effect on steatohepatitis.

Furthermore, model animals of the present invention are characterized in showing diabetic disorders (diabetic nephritis, retinopathy, or such) which develop as a complication of diabetes, simultaneously in conjunction with steatohepatitis. Thus, model animals of the present invention are useful as diabetes model animals.

Specifically, the present invention provides diabetes model non-human animals prepared by administering agents for inducing organ inflammation. Agents for treating or preventing diabetic disorders (diabetic nephritis, retinopathy, or such) can be developed by using diabetes model animals of the present invention. For example, candidate compounds for treating or preventing diabetic disorders can be screened by administering test substances to diabetes model animals of the present invention, and evaluating their ameliorating effect on diabetic disorders.

In a preferred embodiment, the present invention provides methods of screening for substance for treating or preventing diabetic disorders, which comprise the steps of:
(a) administering a test substance to a non-human animal model of diabetic disorder of the present invention; and
(b) evaluating its ameliorating effect on diabetic disorder.

Many NASH patients are also diabetes patients, and they are thought to develop various complications. Model animals of the present invention develop diabetic complications and are thus very useful as model animals, because risks such as side effects discovered at clinical trials can be evaluated at earlier stages by using the model animals.

Specifically, the present invention provides methods for evaluating the side effects risks of pharmaceutical agents by using the diabetes model animals of the present invention.

In a preferred embodiment, the present invention relates to methods for evaluating the risk of side effects of pharmaceutical agents for treating or preventing diabetic disorders, which comprise the steps of:
(a) administering a test pharmaceutical agent to the non-human animal model of diabetic disorder of the present invention; and
(b) evaluating the side effects of the pharmaceutical agent for treating or preventing diabetic disorder.

Furthermore, the present inventors for the first time discovered that as the rearing continues, the above-described steatohepatitis model animals of the present invention develop liver cirrhosis which leads to liver cancer. Thus, the present invention provides liver cirrhosis model animals and liver cancer model animals which are prepared by continuing to rear the above-described steatohepatitis model animals.

In a preferred embodiment, the present invention relates to liver cancer model animals which are prepared by continuing the rearing of steatohepatitis model animals prepared by administering agents for inducing organ inflammation.

The above-described steatohepatitis model animals of the present invention subsequently develop liver cirrhosis. Liver cancer model animals can be produced by further rearing of the animals. In producing such model animals, the period of rearing after liver cirrhosis has developed is typically, for example, 2 to 20 weeks or more, and preferably 10 weeks or more, when the experimental animal is mouse.

Liver cancer model animals of the present invention are structurally characterized, for example, by at least one (preferably, all) selected from the following pathological findings (pathological morphologies):

(a) massive type cord-like liver cell carcinoma;
(b) infiltration of inflammatory cells; and
(c) liver cancer caused by cirrhosis developed such that it displaces normal liver cells.

Liver cancer model animals having the above-described characteristics exhibit the pathological morphologies described above, and thus are structurally different from conventional liver cancer model animals prepared by administering chemical substances (carcinogenic substances).

Substances for treating or preventing liver cancer can be selected by using the above-described liver cancer model animals of the present invention.

In a preferred embodiment, the above-described methods of the present invention includes methods of screening for substances for treating or preventing liver cancer, which comprise the steps of:
(a) administering a test substance to a liver cancer model animal of the present invention; and
(b) evaluating its therapeutic effect on liver cancer.

In the above-described methods, the therapeutic effect can be appropriately evaluated, for example, using as an indicator the above-described pathological findings of liver cancer. For example, when massive type cord-like liver cell carcinoma is eliminated in a model animal of the present invention administered with a test substance, the test substance is judged to have therapeutic effect on liver cancer.

Furthermore, according to the present invention, medicinal substances can be evaluated for their efficacy in liver cancer treatment by using liver cancer model animals of the present invention. In a preferred embodiment, the methods include, for example, those comprising the steps of:
(a) administering a test medicinal substance to a liver cancer model animal of the present invention; and
(b) evaluating its therapeutic effect on liver cancer.

All prior art documents cited herein are incorporated herein by reference.

EXAMPLES

Hereinbelow, the present invention will be described more specifically with reference to the Examples, but it is not limited thereto.

Example 1

Preparation of NASH Model Animals and Liver Cancer Model Animals (a) Preparation of NASH Model Mice Gestational C57BL6J/JJcl, C3H/HeNJcl, and BALB/cByJJcl (CLEA Japan Inc.) and C57BL6J/NCrlCrlj (Charles River Japan, Inc.) were reared and allowed to deliver. Pancreatic inflammation was induced in male mice of C57BL6J/JcL, BALB/cByJJcl, and C3H/HeNJcl (CLEA Japan Inc.) two days after birth with cytotoxicity specific to N-Acetyl-beta-D-glucosaminidase (O-GlcNAcase) in pancreatic β cells (for example, by subcutaneously administering 10 mg/ml streptozotocin (SIGMA) at 20 μl/head). Thus, insulin resistance was induced by directly or indirectly eliciting inflammation in peripheral tissues. The mice were reared with a CE-2 diet (CLEA Japan Inc.) and sterile water until four weeks old, and ablactated when they reached the age of four weeks. Then, the mice were reared until 20 weeks old with sterile water and High Fat Diet (CLEA Japan Inc.) or D12492 (Research Diets), which have a higher crude fat content (or by about 30% or more) than normal diet.

(b) Histological Assessment

Figure 2:
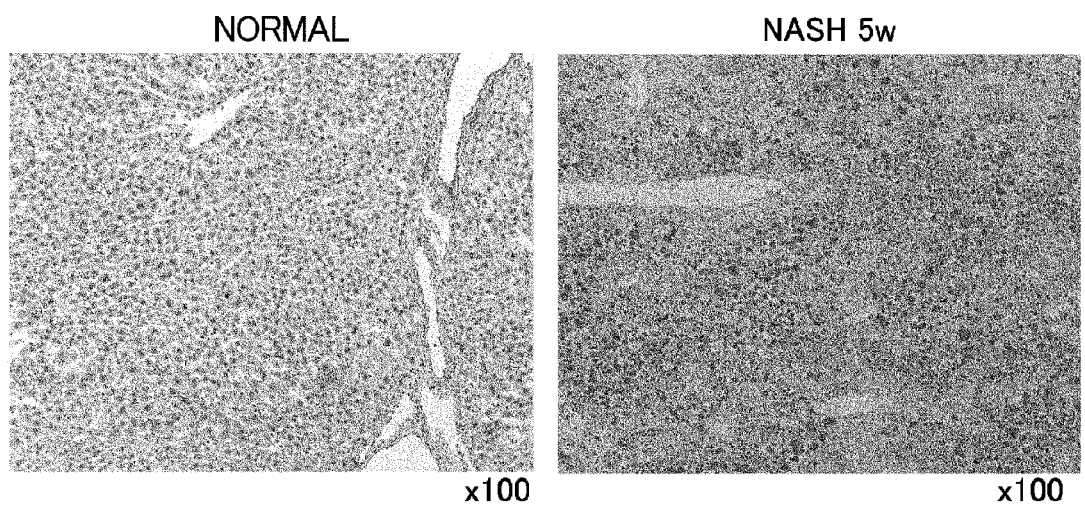
FIG. 2 shows in photographs a result of fat staining of liver from a mouse of the present invention.
Figure 3:
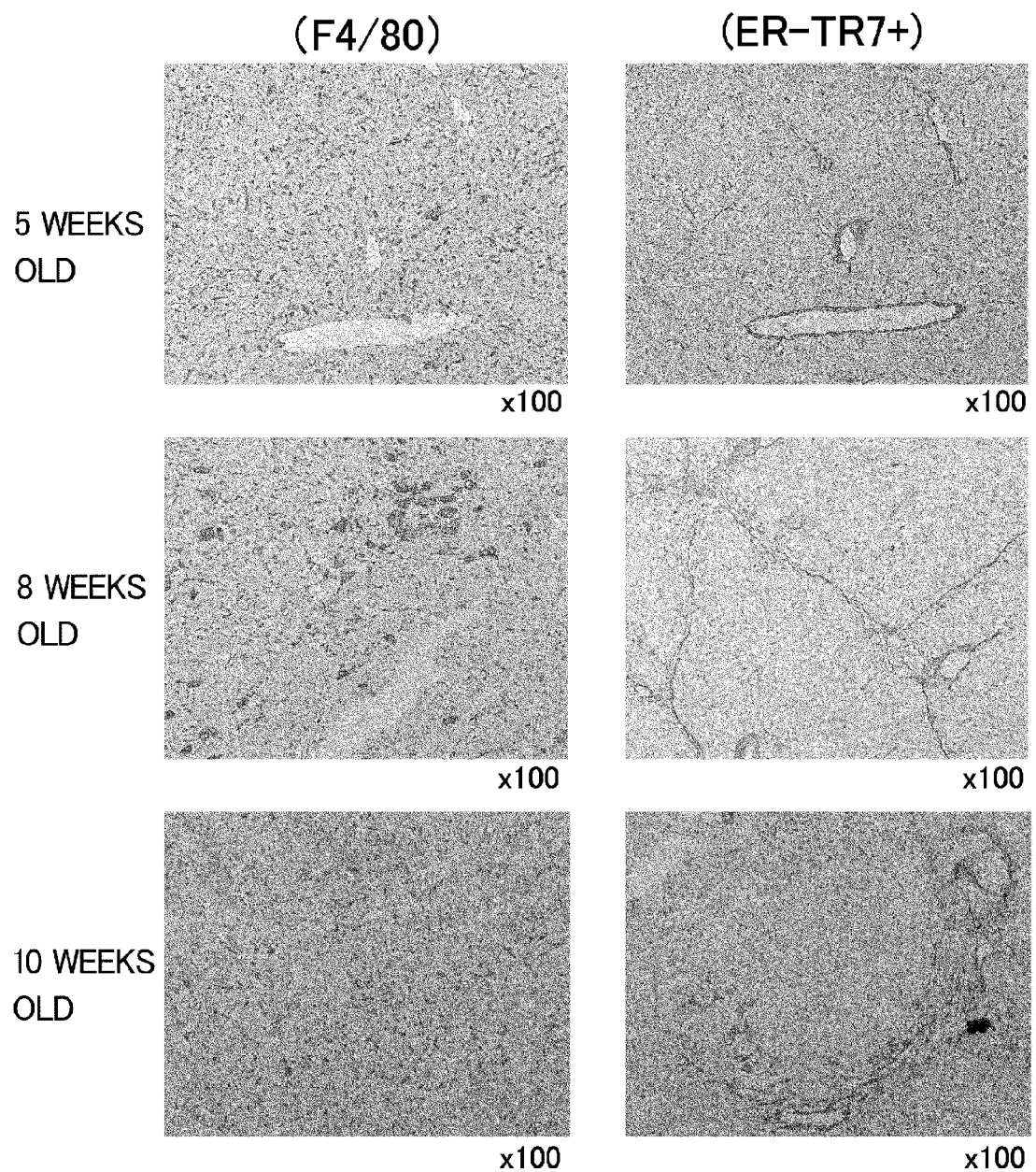
FIG. 3 shows in photographs a result of immunostaining of liver from a mouse of the present invention.
Figure 5:
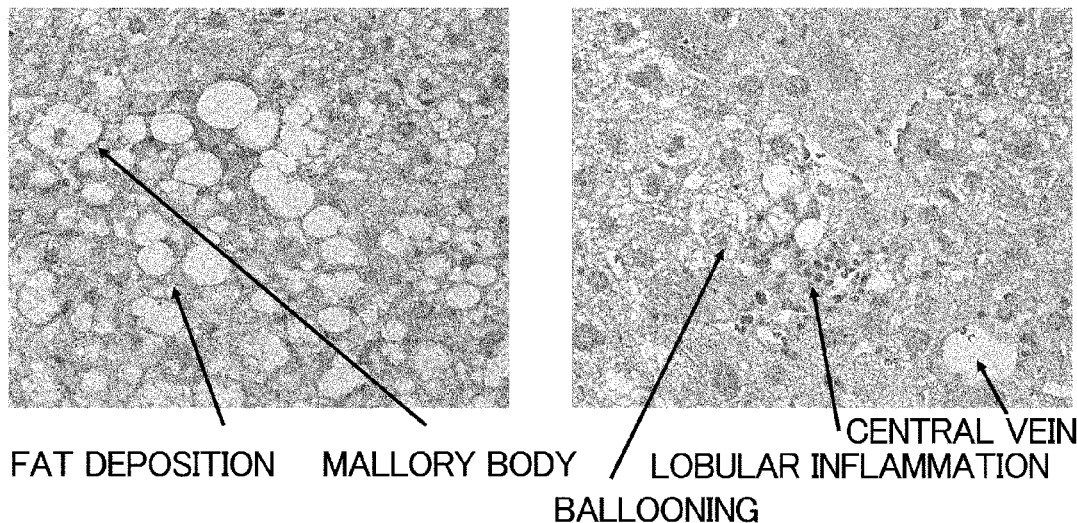
FIG. 5 shows a result of HE staining of liver from C57BL/6J in photographs and the NAFLD Activity Score in a graph.
Figure 5:
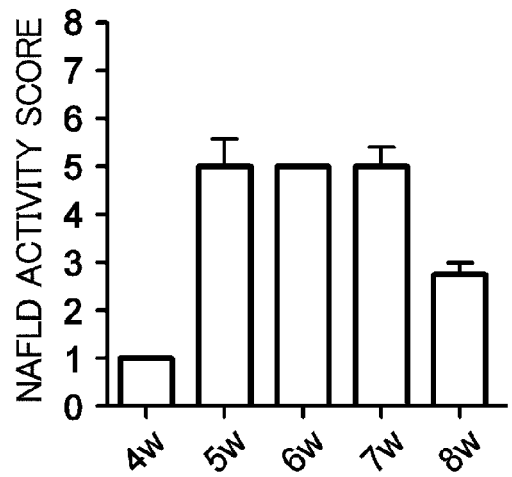

After mice of different ages were fasted for 24 hours, they were sacrificed under ether anesthesia, and blood was collected. Each organ was frozen in OCT compound (Sakura Fine Technical), and then sliced into sections for pathological analysis. A serobiochemical test showed that the levels of fasting blood glucose, alanine aminotransferase (ALT), and neutral fat were all higher in this model as compared to the group of normal animals. Thus, the model animals developed insulin resistance and hyperlipemia (FIG. 1). Histologically, severe fatty liver with liver cell ballooning was observed at the age of five weeks. Fat was almost completely eliminated from the liver at the age of eight weeks, and thus the progression of histopathological condition was very similar to that of human burned-out NASH (FIG. 2). At the age of six weeks, accumulation and infiltration of inflammatory cells including macrophages was observed in their liver, and fibrosis progressed around the central vein of liver. Result obtained by further observation of changes over time showed that at the age of eight weeks, central veins become connected as fibrosis progressed, and liver cirrhosis with formation of regenerating nodules was observed at the age of ten weeks (FIG. 3). Furthermore, NAS was calculated based on the histopathological data. The result showed that the score was 5 in average at the NASH stage. Thus, it was demonstrated that the pharmacological effect could be evaluated by monitoring changes of this score (FIG. 5).

Figure 4:
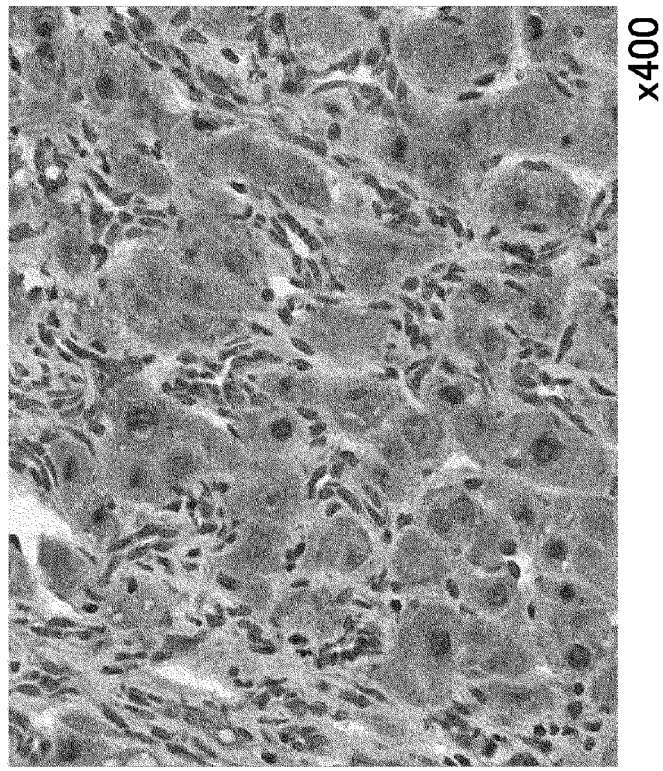
FIG. 4 shows in photographs a result of HE staining of liver from a 20-week-old mouse of the present invention.
Figure 4:
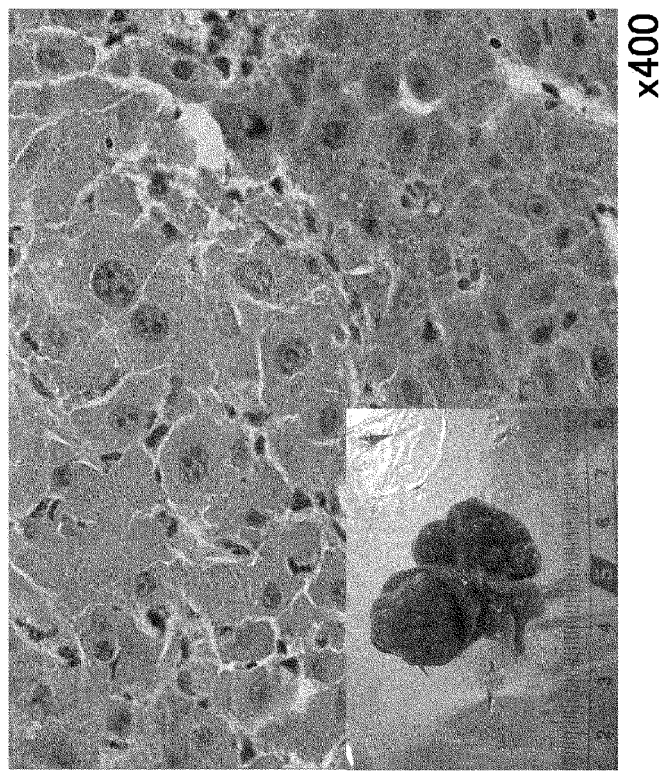
Figure 6:
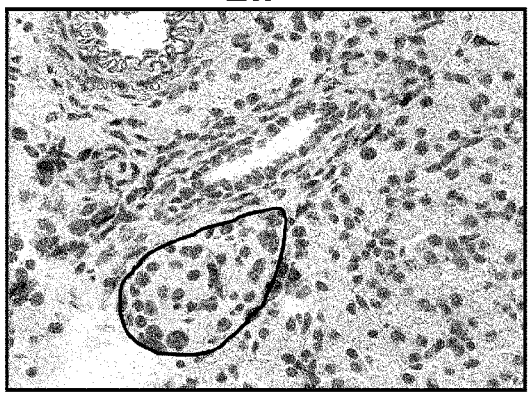
FIG. 6 shows in photographs a result of F4/80 immunostaining of pancreas and adipose tissue from C57BL/6J.
Figure 6:
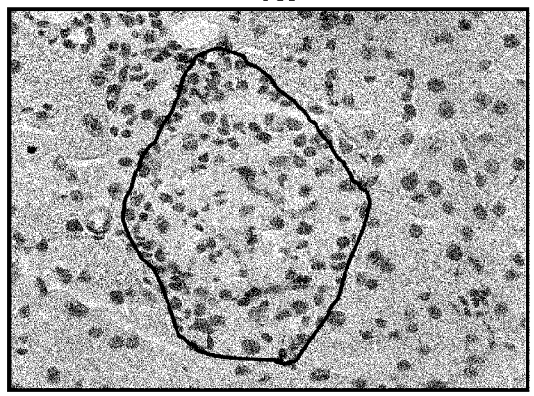
Figure 6:
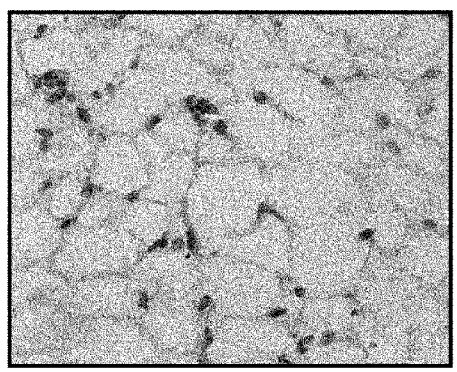
Figure 6:
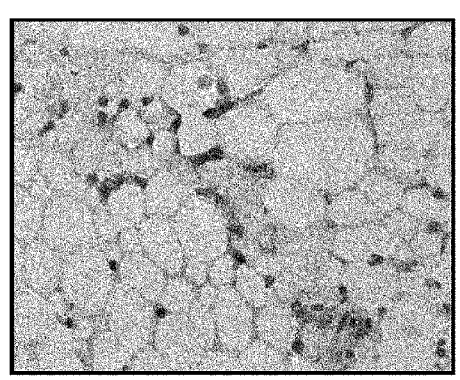
Figure 6:
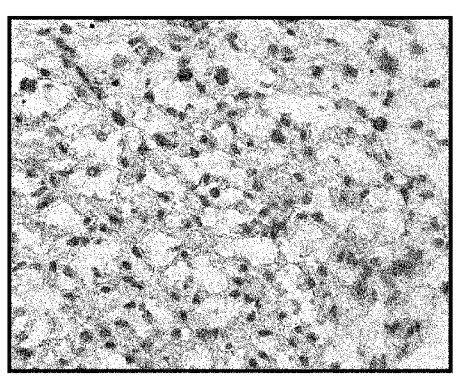
Figure 7:
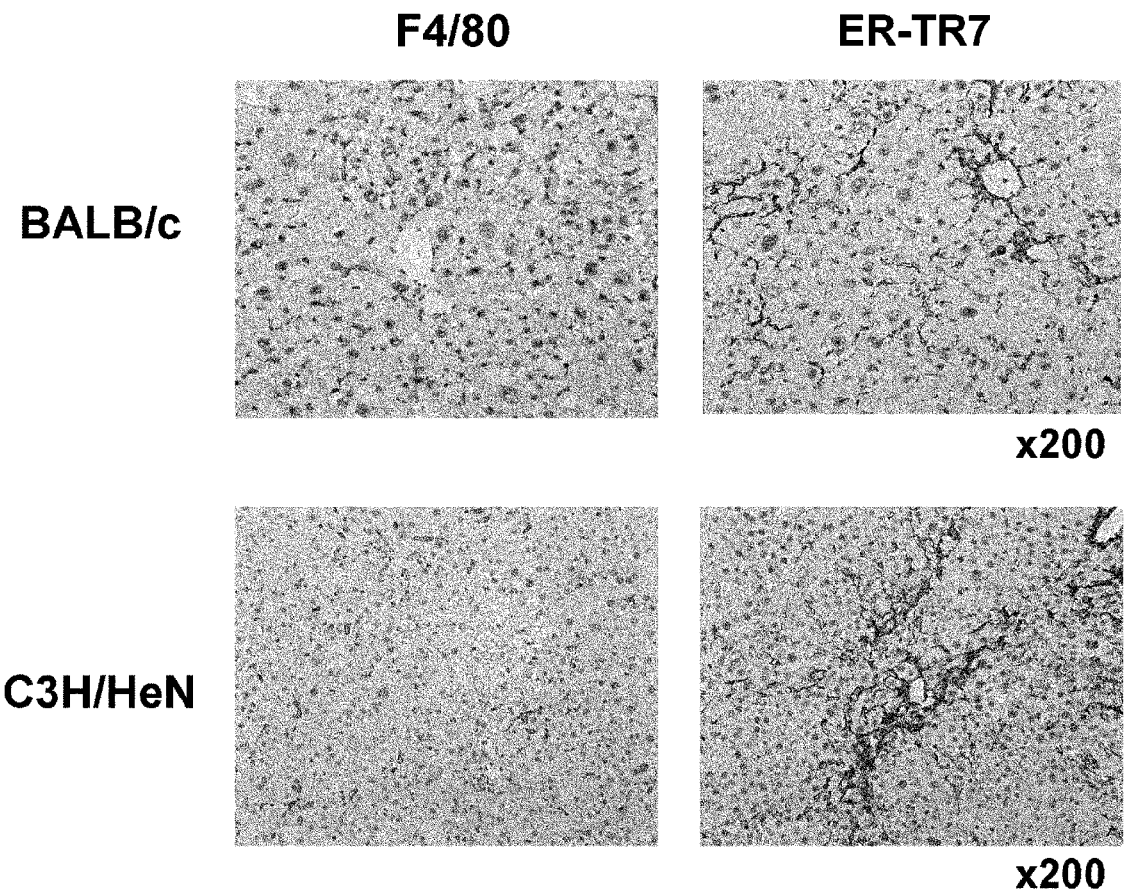
FIG. 7 shows in photographs a result of immunostaining of F4/80 and ER-TR7 of 8-week-old BALB/c and C3H/HeN mice.
Figure 8:
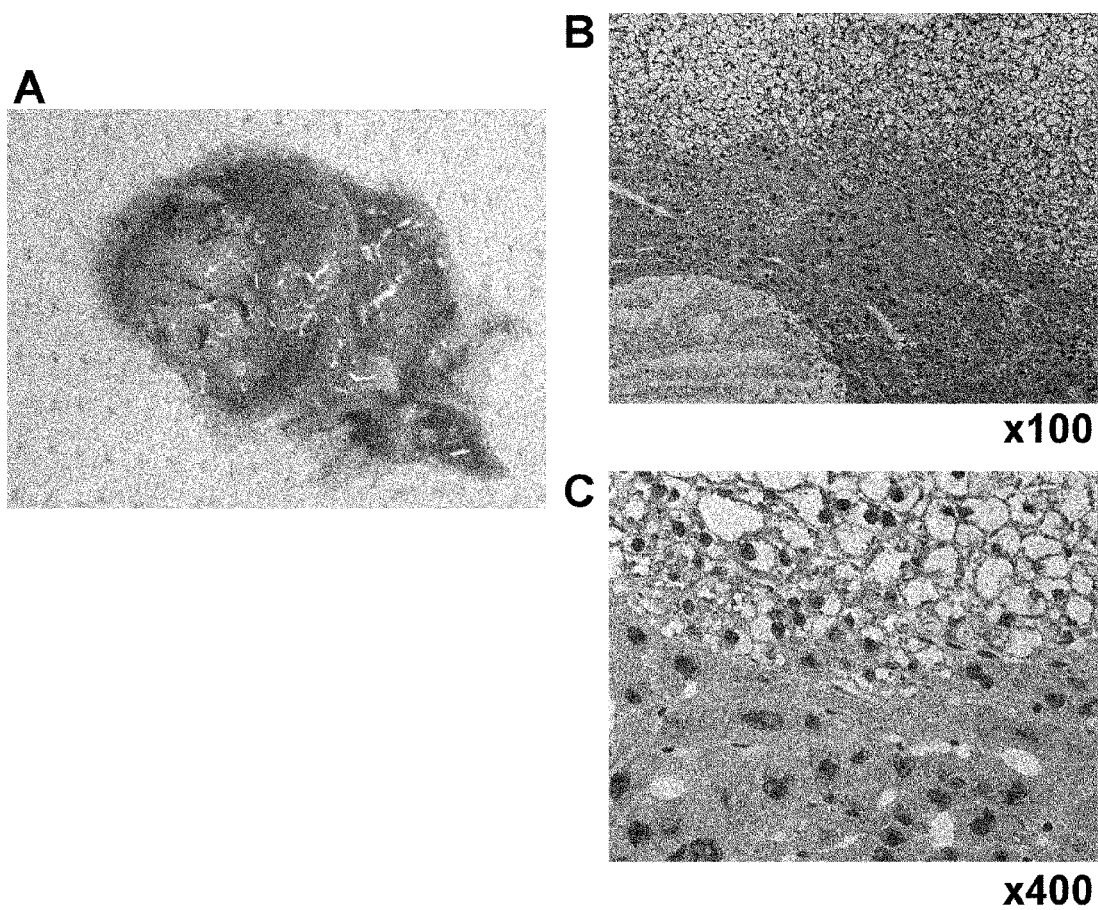
FIG. 8 shows photographs of liver cancer in 20-week-old C3H/HeN.
Figure 9:
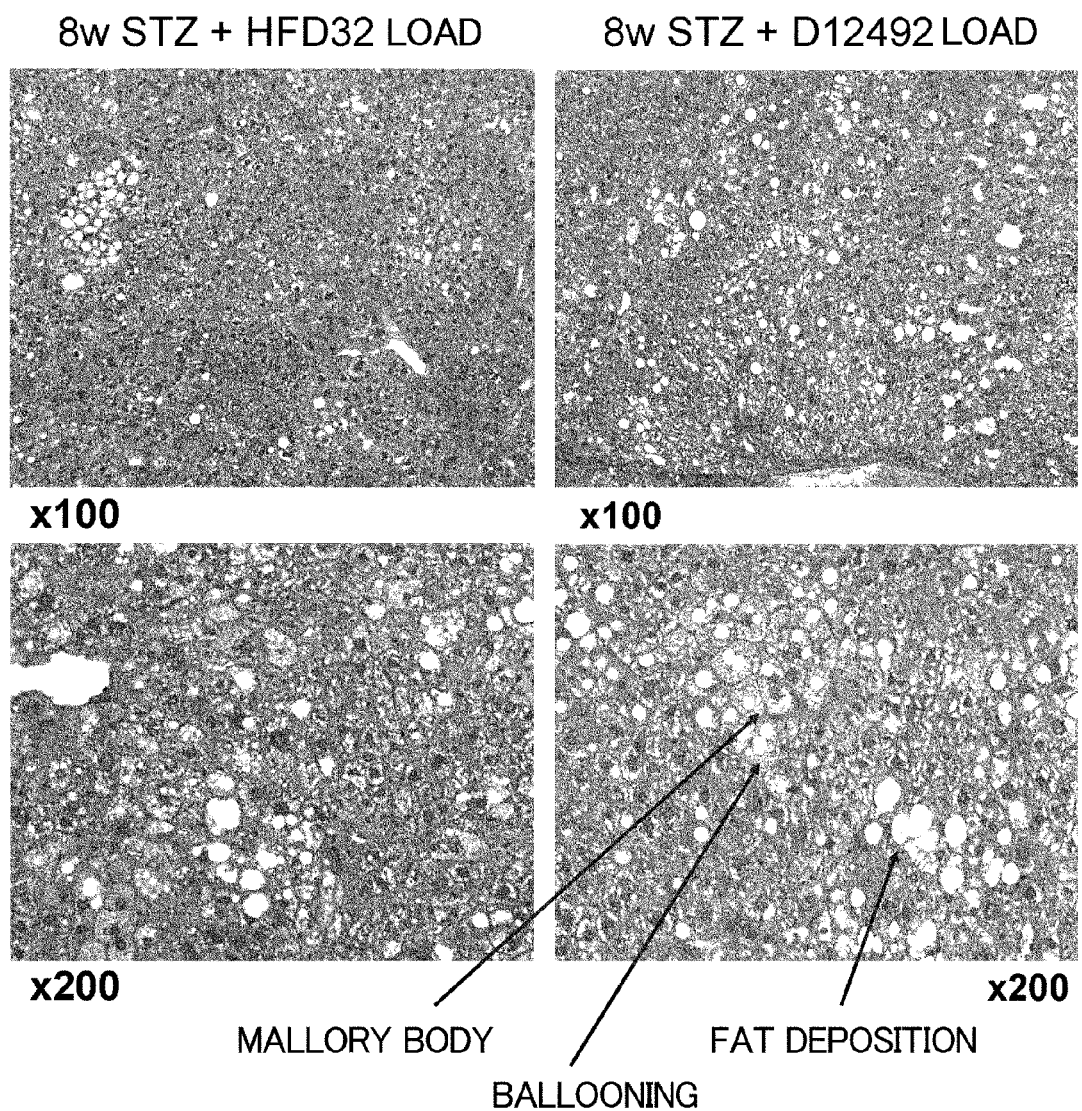
FIG. 9 shows in photographs reproducible results of NASH model mice reared with other high fat diets.

The pathogenesis of NASH in this mouse model is that pancreatic inflammation triggers chronic inflammation in peripheral tissues such as liver and adipose tissues; insulin resistance develops; and persistent systemic inflammation leads to fatty liver (FIG. 6). Then, the regenerating nodules enlarged as the mice age. Infiltration of inflammatory cells, increase of atypical hepatocytes, and development of cancer to displace normal liver cells were observed at the age of 20 weeks (FIG. 4). Moreover, lesions that are histologically consistent with NASH lesion which leads to liver cancer can also be developed in mice of other lines (FIGS. 7 and 8). NASH lesions were reproducible even if the type of high fat diet was changed (FIG. 9).

Figure 10:
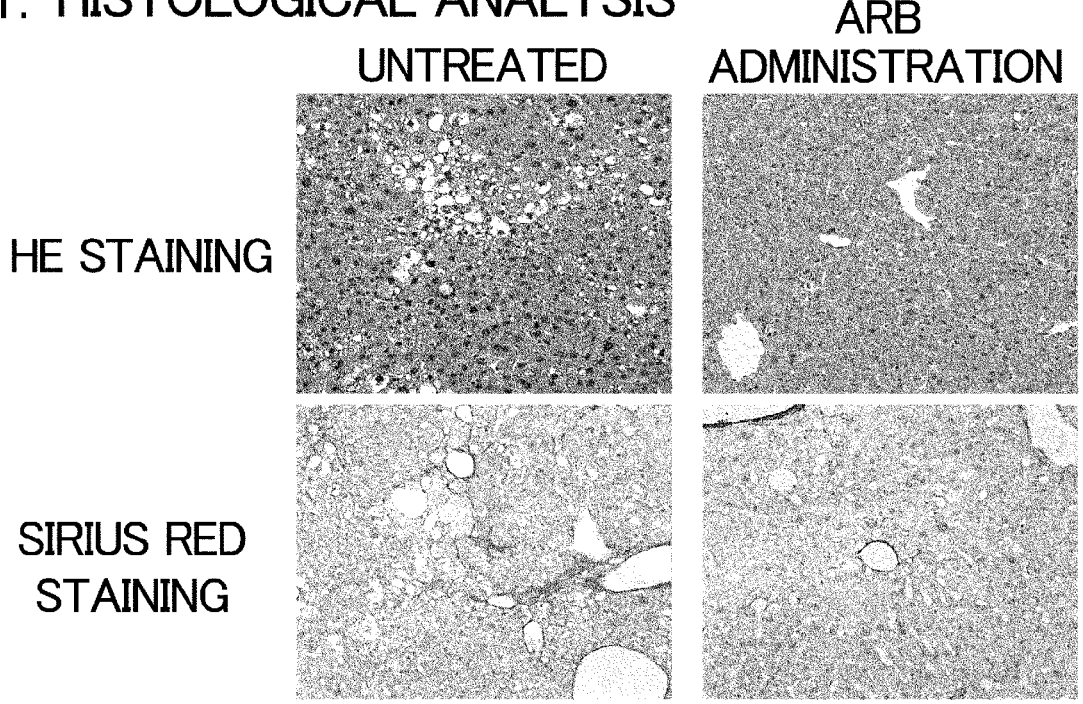
FIG. 10 shows in photographs and graphs results of pharmacological tests using the NASH model mice. 1 shows the result of histological analysis in photographs. 2 shows the result of gene expression analysis in photographs.
Figure 10:
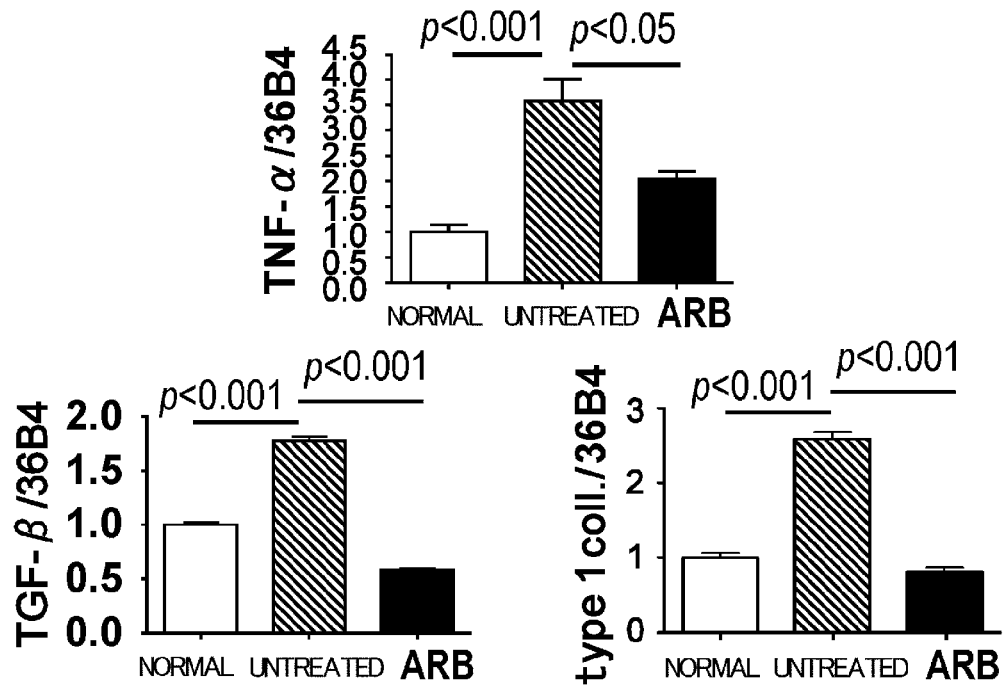

Furthermore, as a trial of NASH therapy, angiotensin receptor antagonist (ARB), which is an antihypertensive agent, was orally administered to the model of the present invention for two weeks. Consistent with a clinical report (Georgescu E. F. et al., 15: 942), comparison of the ARB-administered group and the non-treated group showed histological improvement in the liver and ameliorating effects on inflammation and fibrosis as detected by genetic test, which suggested, the result is highly similar to clinical results (FIG. 10).

Figure 11:
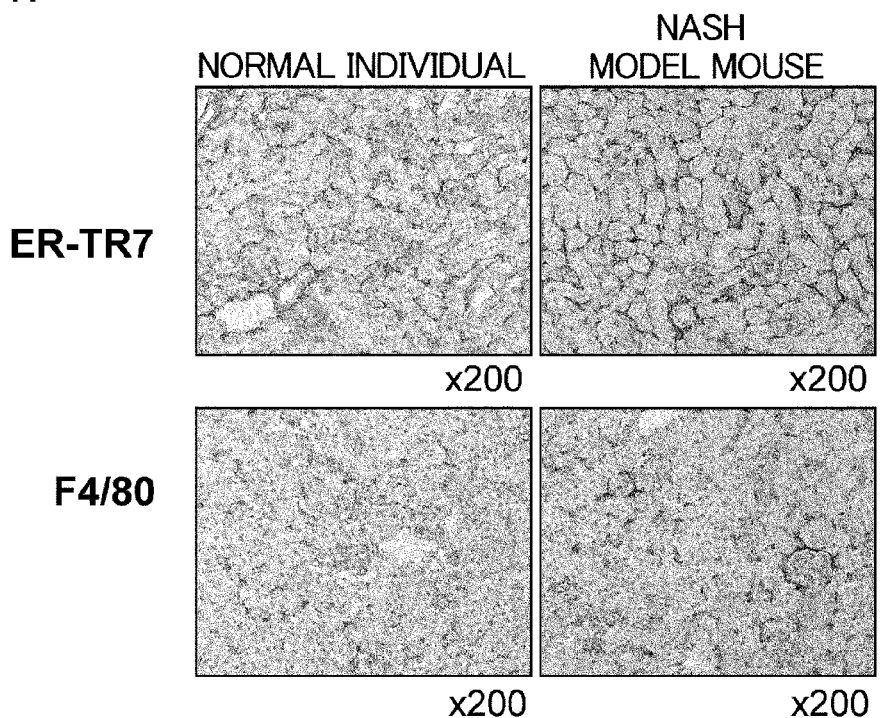
FIG. 11 shows the onset of diabetic complications in photographs. 1 shows diabetic nephropathy in photographs, while 2 shows diabetic retinopathy (immunostaining images of new blood vessels; CD31) in photographs.
Figure 11:
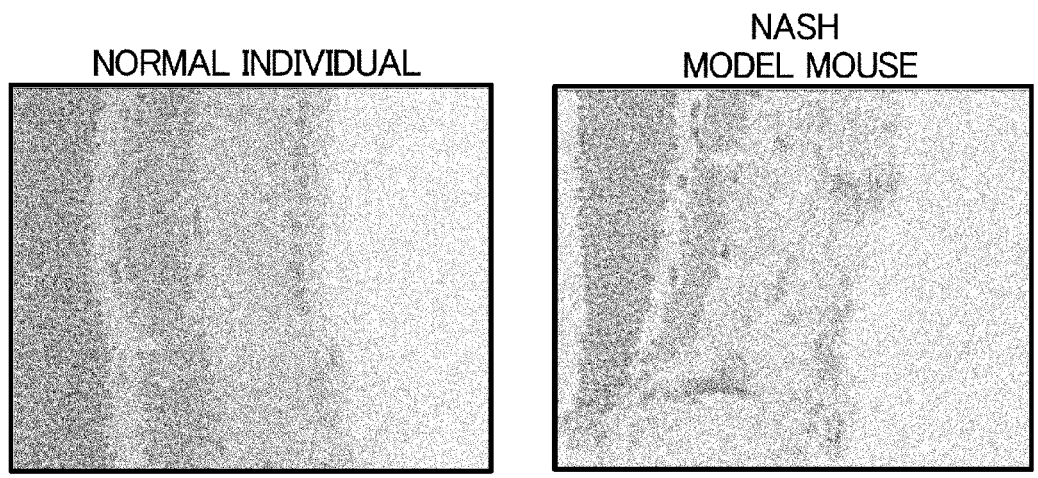

Furthermore, in the mouse model of the present invention, adipose tissue inflammation is also induced at the same time and this potentiates insulin resistance. The resulting persistent chronic hyperglycemia causes microangiopathy and such, leading to diabetic complications (diabetic nephropathy, retinopathy, and neuropathy). Then, pathological lesions in other organs were studied in detail. As a result, glomerular and interstitial fibrosis which are characterized by accumulation of inflammatory macrophages and fibroblasts within and around renal glomeruli were observed at the age of ten weeks, and thus the animals developed diabetic nephropathy (FIG. 11). Furthermore, at the age of 20 weeks, neovascularization in the eyes was assessed using a CD31 antibody. In the model mice of the present invention, neovascular blood hyperplasia was observed in the retina, suggesting that the mice developed diabetic retinopathy (FIG. 11).

Thus, the present invention provides NASH model animals which develop fatty liver leading to liver cancer. The use of such model animals facilitates the analysis of pathogenesis and pathological condition of human NASH, and development of techniques and agents for treating human NASH.

INDUSTRIAL APPLICABILITY

The causes of fat accumulation in the liver include alcohol, obesity, diabetes, lipid metabolism abnormality, pharmaceutical agents, and severe malnutrition. However, the causes are roughly categorized as alcoholic and nonalcoholic. Alcoholic fatty liver leads to hepatitis, liver fibrosis, and liver cirrhosis. Meanwhile, nonalcoholic fatty liver has been believed to be a pathological condition that does not progress. However, in the late 1990s, as the obese population increased and the disease concept became known, it was revealed that nonalcoholic fatty liver is a high-incidence disease next to type C hepatitis and alcoholic hepatitis in Europe and the United States. The pathological condition was reported to progress into liver cirrhosis and finally liver cancer, which drew attention to the disease. In Japan, the obese population with obesity is also steadily increasing due to genetically predisposed low insulin secretion, and westernized diets and lack of physical activity. Under such circumstances, the number of patients diagnosed as NASH is increasing, and thus there is an urgent demand for developing and establishing methods and agents for treating NASH.

The model of the present invention is highly similar to the pathological condition of human NASH in terms of disease progression, and can be used to determine the stage for analyzing the phases of insulin resistance, fatty liver, steatohepatitis, liver fibrosis, and liver cirrhosis, depending on the subject to be treated. Furthermore, by searching for pathogenic factors involved in the progression of each phase, the present invention can also contribute to the development of completely new methods or agents for treating human NASH, hepatic fibrosis, and liver cirrhosis, as well as biomarkers for the diseases. In addition, the present invention is applicable to evaluate pharmacokinetics in NASH lesions. Moreover, the model of the present invention finally leads to liver cancer. Thus, the present invention enables the screening for cancer-suppressing agents or such, investigation of onset mechanism for liver cancer, and pharmaceuticals that target molecules in development of liver cancer.

In addition to the diseases described above, diabetic disorders can also be analyzed at the same time. Thus, the present invention is expected to greatly contribute to the development of methods and agents for liver diseases, elucidation of the relationships among systemic pathological conditions in a subject animal, as well as development of therapeutic methods/agents and biomarkers.

The invention claimed is:
1. A non-human animal model, which is produced by:
 (a) administering to a non-human mammal of one to five days old an N-acetyl-β-D-glucosaminidase inhibitor in an amount sufficient to induce organ inflammation wherein the inhibitor is selected from the group consisting of streptozotocin and Pugnac;
 (b) rearing the mammal with a high-fat diet over a period of time sufficient to induce liver cirrhosis; and

(c) further rearing the mammal with a high-fat diet over a period of time sufficient to induce liver cancer caused by cirrhosis, developed such that it displaces normal liver cells of the mammal.

2. The non-human animal model of claim 1, wherein the non-human mammal is a mouse.

3. The non-human animal model of claim 1, wherein, in step (a), the mammal is two days old.

4. The non-human animal model of claim 1, wherein the ratio of fat-derived calories to total calories of the high-fat diet is 50% or more.

5. A non-human animal model, which is produced by:
(a) administering to a non-human mammal of one to five days old an N-acetyl-β-D-glucosaminidase (O-GlcNAcase) inhibitor in an amount sufficient to induce organ inflammation wherein the inhibitor is a nucleic acid sequence suppressing expression of an O-GlcNAcase gene;
(b) rearing the mammal-with a high-fat diet over a period of time sufficient to induce liver cirrhosis; and
(c) further rearing the mammal with a high-fat diet over a period of time sufficient to induce liver cancer caused by cirrhosis, developed such that it displaces normal liver cells of the mammal.

6. The non-human animal model of claim 5, wherein the non-human mammal is a mouse.

7. The non-human animal model of claim 5, wherein, step (a), the mammal is two days old.

8. The non-human animal model of claim 5, wherein the ratio of fat-derived calories to total calories of the high-fat diet is 50% or more.

9. The non-human animal model of claim 5, wherein the nucleic acid sequence is an siRNA sequence.

10. The non-human animal model of claim 5, wherein the nucleic acid sequence is an antisense sequence.

11. The non-human animal model of claim 5, wherein the nucleic acid sequence is a ribozyme that targets an O-GlcNAcase gene.

\* \* \* \* \*